US012653869B2

(12) United States Patent
Schulze Zur Wiesche et al.

(10) Patent No.: US 12,653,869 B2
(45) Date of Patent: Jun. 16, 2026

(54) COMPOSITION FOR TREATMENT AND/OR PREVENTION OF A CORONA VIRUS INFECTION

(71) Applicant: Dr. Kurt Wolff GmbH & Co. KG, Bielefeld (DE)

(72) Inventors: Erik Schulze Zur Wiesche, Bielefeld (DE); Miriam Stark, Bielefeld (DE); Eduard Richard Doerrenberg, Bielefeld (DE)

(73) Assignee: Dr. Kurt Wolff GmbH & Co. KG, Bielefeld (DE)

( * ) Notice: Subject to any disclaimer, the term of this patent is extended or adjusted under 35 U.S.C. 154(b) by 393 days.

(21) Appl. No.: 18/550,098

(22) PCT Filed: Mar. 11, 2022

(86) PCT No.: PCT/EP2022/056340
§ 371 (c)(1),
(2) Date: Sep. 11, 2023

(87) PCT Pub. No.: WO2022/189630
PCT Pub. Date: Sep. 15, 2022

(65) Prior Publication Data
US 2024/0148838 A1     May 9, 2024

(30) Foreign Application Priority Data
Mar. 12, 2021     (EP) ..................................... 21162437

(51) Int. Cl.
| | |
|---|---|
| *A61K 38/40* | (2006.01) |
| *A61K 9/00* | (2006.01) |
| *A61K 31/4015* | (2006.01) |
| *A61K 33/30* | (2006.01) |
| *A61K 47/18* | (2017.01) |
| *A61K 47/20* | (2006.01) |
| *A61K 47/26* | (2006.01) |
| *A61K 47/38* | (2006.01) |
| *A61P 31/14* | (2006.01) |

(52) U.S. Cl.
CPC .............. *A61K 38/40* (2013.01); *A61K 9/006* (2013.01); *A61K 31/4015* (2013.01); *A61K 33/30* (2013.01); *A61K 47/18* (2013.01); *A61K 47/20* (2013.01); *A61K 47/26* (2013.01); *A61K 47/38* (2013.01); *A61P 31/14* (2018.01)

(58) Field of Classification Search
CPC ................................ A61K 38/40; A61P 31/14
See application file for complete search history.

(56) References Cited

FOREIGN PATENT DOCUMENTS

| | | |
|---|---|---|
| CN | 101938987 A | 1/2011 |
| CN | 104822361 A | 8/2015 |
| CN | 116615180 A | 8/2023 |
| EP | 1040819 A2 | 10/2000 |
| WO | WO 2009/100269 A2 | 8/2009 |
| WO | WO 2014/088573 A1 | 6/2014 |

OTHER PUBLICATIONS

Extended European Search Report, issued in corresponding EP application No. 25 180 934.9, dated Jul. 9, 2025, 7 pages.
International Search Report and Written Opinion mailed May 30, 2022 in International Application No. PCT/EP2022/056340, 13 pp.
Meister et al. (Jul. 2020) "Virucidal efficacy of different oral rinses against severe acute respiratory syndrome Coronavirus 2," J Infect Dis. Volume 222, Issue 8, 1289-1292. https://doi.org/10.1093/infdis/jiaa471.
Moosavi et al. (Jan. 2020) "Antiviral mouthwashes: possible benefit for COVID-19 with evidence-based approach," Journal of Oral Microbiology, 12:1, 1794363. DOI: 10.1080/20002297.2020.1794363.
Notification pursuant to Article 94(3) EPC, for corresponding application No. EP 22 713 941.7, dated Aug. 2, 2024.
Chinese Office Action, issued in corresponding CN application No. 202280020073.X, dated Apr. 10, 2026, 12 pages.

*Primary Examiner* — Amber D Steele

(74) *Attorney, Agent, or Firm* — Leydig, Voit & Mayer, LTD.

(57) ABSTRACT

The invention relates to a topical composition having a low anionic surfactant amount for use in the treatment and/or prevention of a corona virus infection.

20 Claims, No Drawings

COMPOSITION FOR TREATMENT AND/OR PREVENTION OF A CORONA VIRUS INFECTION

CROSS-REFERENCE TO RELATED APPLICATIONS

This application is a U.S. National Stage Application filed under 35 U.S.C. § 371 of International Application No. PCT/EP2022/056340, filed Mar. 11, 2022, which claims the benefit of European Patent Application No. 21162437.4, filed Mar. 12, 2021. Both of these applications are hereby incorporated by reference in their entireties.

FIELD OF THE INVENTION

The present invention is directed to a topical composition having a low total surfactant amount, in particular a low total anionic surfactant amount, for the treatment and/or prevention of a corona virus infection.

BACKGROUND OF THE INVENTION

Viruses belonging to the family of Coronaviridae were first characterized in the 1960's. Virus infections belonging to this family are common in all mammal species including humans. The SARS-CoV-2 outbreak made it evident that novel pharmaceutical compositions are needed to treat and prevent the widespread of virus infections in general, and in particular infections with the SARS-CoV-2.

Corona viruses are RNA viruses with a linear ss-RNA (single-stranded RNA) that are transmitted via droplet infection and result i.a. in fever and respiratory problems. There are several species that are relatively harmless and result in only acute and mild symptoms or take an asymptomatic course (HCoV-OC43, 229E, HKU1, and HL63). On the other hand, SARS-CoV (Severe Acute Respiratory Syndrome Corona Virus), MERS-CoV (Middle East Respiratory Syndrome Corona Virus) and SARS-CoV-2 are Corona viruses that can lead to severe respiratory and lung infections. So far there are only very limited treatment or prophylaxis options, except for exposure prophylaxis. Some mouth rinse compositions have been investigated in vitro by Steinmann et al., The Journal of Infectious Diseases 2020, XX, pp 1-4 for the activity against SARS-CoV-2.

In view of the above, it was an object of the present invention to provide a novel, safe, and effective composition for the treatment and/or prevention of a corona virus infection in general and in particular for the treatment and/or prevention of a SARS-CoV-2 infection.

SUMMARY OF THE INVENTION

These objects have surprisingly been solved by a composition comprising at least two anionic surfactants A and B in a weight ratio NB from 10/1 to 1.1/1, wherein surfactant A is an alkyl sulfate and surfactant B is selected from alkyl sulfates, alkyl sarcosinates, and alkyl taurates, wherein the total amount of anionic surfactants in the composition is 1 wt.-% or less.

It has surprisingly been found that according to the above aspect, infections with a virus can be prevented or the probability of infection can at least significantly be reduced. In addition, and in accordance with the above aspect, the virus count in the respiratory tract is significantly reduced so that an infected person is no longer infectious towards third persons.

In another aspect, the present invention relates to a composition comprising 0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof, 0.001 to 1 wt.-% of a total amount of anionic surfactants, comprising at least two anionic surfactants A and B in a weight ratio NB from 10/1 to 1.1/1, wherein surfactant A is an alkyl sulfate and surfactant B is selected from alkyl sulfates, alkyl sarcosinates, and alkyl taurates, and 0.001 to 5 wt.-% of a polyalcohol selected from erythritol, arabitol, lactitol, maltitol, mannitol, sorbitol, xylitol, and mixtures thereof.

The present invention also relates to a kit of parts comprising the composition of the present invention, and a spraying device or a mouth rinse device or a gargling device, for applying the composition to the mucous membranes of the nose, mouth (oral cavity) and/or throat (pharynx).

DETAILED DESCRIPTION

The following definitions are relevant in connection with the embodiments of the present invention.

The meaning of the term "comprising" is to be interpreted as encompassing all the specifically mentioned features as well optional, additional, unspecified ones, whereas the term "consisting of" only includes those features as specified. Therefore, "comprising" includes as a limiting case the composition specified by "consisting of".

The term "weight-%" or "wt.-%" is to be understood to refer to the weight amount of the component relative to the total weight amount of the respective composition, if not specified otherwise.

The term "water-soluble" refers to a zinc salt that has a solubility of 0.1 g/L or more at standard conditions. Correspondingly, the term "water-insoluble" refers to a zinc-salt that has a solubility of less than 0.1 g/L at standard conditions, i.e. at a temperature of 15° C. and a pH value of 7.0.

The term "film-forming" polymer refers to a polymer that results in a cohesive, continuous layer when applied to a surface. In the present invention, when the composition is applied topically to the mucous membrane, the film-forming polymer leads to the formation of a cohesive layer of the composition that further has enhanced adhesive properties to the mucous membrane.

As used herein, the term "prevention" of a corona virus infection (also named prophylaxis), on the one hand, refers to prevention of a (local) infection in a subject that had contact with the virus. On the other hand, the term "prevention" also refers to the prevention of passing the infection on to further subjects, in case the subject that uses the composition is already infected with the virus. In other words, the composition in general effectively prevents infection with the corona virus and/or a further transfer or distribution of the corona virus e.g. by aerosol/droplet spreading. Thus, a dual method of preventing widespread of the virus is achieved by the composition of the present invention.

Both "treatment" and "prevention" of a corona virus infection according to the invention are based on the composition's antiviral activity so that the virus count (virus load) is decreased in the mouth, throat and nasal area (i.e. in the upper respiratory tract), thereby resulting in an effective local treatment of the virus, as the virus is predominately located in these areas. It is believed that the virus count, in particular in the throat, is effectively reduced by using the composition of the invention, even before the virus is able to enter the host cells through the ACE2 receptors and cause an infection. After application the compositions of the invention are effective in decreasing the virus count in mouth, nose and/or throat areas (i.e. in the upper respiratory tract) by up to 99%, preferably up to 95%, more preferably up to 93%, such as up to 90%. It was surprisingly found that this efficacy is maintained for more than 6 hours starting with administration of the composition, preferably 1 to 6 hours, more preferably 1 to 4 hours. In other words, the compositions of the invention are effectively preventing a corona virus infection for more than 6 hours, preferably up to 6 hours, at least for 3 or 4 hours. Thus, the compositions allow an ongoing or sustained reduction of the virus count over quite a long time. At least during that time period the composition of the invention effectively prevents a (local) infection and also avoids passing the infection on to further subjects, i.e. the composition effectively prevents infection with the corona virus and/or a further transfer or distribution of the corona virus in particular by aerosol/droplet spreading. Without wishing to be bound by theory it is assumed that the composition containing the anionic surfactants is effective in destroying and/or deactivating and/or dissolving the outermost protective layer (viral envelope) of the corona virus. In other words, the composition effectively disrupts the viral envelope integrity. Overall the compositions of the present invention provide for a highly effective corona virus infection treatment and/or prevention strategy, in particular with respect to a SARS-CoV-2 infection (such as COVID-19).

Preferred embodiments according to the invention are defined hereinafter. The preferred embodiments are preferred alone or in combination. Further, it is to be understood that the following preferred embodiments refer to all aspects of the present invention, i.e. the composition for use, the composition, and the kit of parts.

In an embodiment, the invention relates to a composition comprising at least two different anionic surfactants A and B in a weight ratio NB from 10/1 to 1.1/1, wherein surfactant A is an alkyl sulfate and surfactant B is selected from alkyl sulfates, alkyl sarcosinates, and alkyl taurates, wherein the total amount of anionic surfactants in the composition is 1 wt.-% or less, for use in the treatment and/or prevention of a corona virus infection. Preferably, surfactant B is selected from alkyl sarcosinates and alkyl taurates, more preferably surfactant B is an alkyl taurate.

In an embodiment the composition further comprises an anionic surfactant C (different from surfactants A and B, respectively) selected from alkyl sulfates, alkyl sarcosinates, and alkyl taurates. In other words, the composition of the invention preferably comprises at least (preferably exactly) three different anionic surfactants A, B, and C, wherein surfactant A is an alkyl sulfate and surfactants B and C are selected from alkyl sulfates, alkyl sarcosinates, and alkyl taurates, more preferably surfactants B and C are selected from alkyl sarcosinates and alkyl taurates, even more preferably surfactant B is an alkyl taurate and surfactant C is an alkyl sarcosinate. Preferably the weight ratio NC is from 16/1 to 1.1/1.

The composition preferably has a total amount of anionic surfactants in the composition of from 0.001 to 1 wt.-%, more preferably 0.01 to 0.9 wt.-%, even more preferably any of the following ranges: 0.05 to 0.8 wt.-%, 0.1 to 0.7 wt.-%, 0.15 to 0.60 wt.-%, 0.20 to 0.50 wt.-%, 0.25 to 0.45 wt.-%. It was surprisingly found that the compositions are effective even with such a low total amount of anionic surfactants.

According to the invention, the anionic surfactants A, B, and C are alkyl sulfates, alkyl sarcosinates, alkyl taurates, and mixtures thereof. It is to be understood by the person skilled in the art that the above terms refer to charge neutral compounds containing a counter cation M, such as sodium.

Alkyl sulfates have the formula $ROSO_3M$, alkyl sarcosinates have the formula $RC(O)N(CH_3)CH_2CO_2M$, and alkyl taurates have the formula $RC(O)N(CH_3)CH_2CH_2SO_3M$, wherein R is a $C_4$-$C_{26}$ alkyl or $C_4$-$C_{26}$ alkenyl, and M is a water-soluble cation such as ammonium, sodium, potassium or triethanolamine. Preferably, R is $C_{12}$-$C_{16}$ alkyl or $C_{12}$-$C_{18}$ alkenyl.

According to the invention, the anionic surfactants in the composition preferably are: sodium lauryl sulfate as surfactant A, sodium methyl cocoyl taurate as surfactant B, and sodium myristoyl sarcosinate as surfactant C. Even if other anionic surfactants may additionally be present, most preferably no other anionic surfactant is contained in the composition.

Preferably the weight ratio of surfactant A to surfactant B as specified herein (ratio A/B) is from 9/1 to 1.1/1, 8/1 to 1.1/1, or 7/1 to 1.1/1. In a particularly preferred embodiment, the weight ratio NB is from 6/1 to 1.5/1, more preferably from 5/1 to 2/1, even more preferably from 4/1 to 2.5/1, most preferably about 3/1. Within these ranges the compositions of the invention are surprisingly significantly effective in the treatment and/or prevention of corona virus infections.

Even preferably the weight ratio of surfactant A to surfactant C, if contained, as specified herein (ratio NC) is from 27/1 to 1.1/1, 26/1 to 1.1/1, 25/1 to 1.1/1, 20/1 to 1.1/1, 16/1 to 1.1/1, 15/1 to 1.1/1, or 14/1 to 1.1/1. In a particularly preferred embodiment, the weight ratio NC is from 13/1 to 2/1, more preferably from 12/1 to 5/1, even more preferably from 11/1 to 8/1, most preferably about 10/1. Within these ranges the compositions of the invention are surprisingly significantly effective in the treatment and/or prevention of corona virus infections.

In a particularly effective embodiment the weight ratio of all three surfactants A, B, and C (ratio A/B/C) preferably is about 30/10/3 or about 80/10/3.

Surfactant A, namely an alkyl sulfate, preferably sodium lauryl sulfate, is contained in the composition preferably within a range of 0.001 to 0.8 wt.-%, more preferably 0.01 to 0.5 wt.-%, even more preferably 0.1 to 0.4 wt.-%, most preferably 0.2 to 0.3 wt.-%.

Surfactant B, namely an alkyl sulfate, alkyl sarcosinate, or alkyl taurate, preferably an alkyl sarcosinate or an alkyl taurate, most preferably sodium methyl cocoyl taurate, is contained in the composition preferably within a range of 0.001 to 0.5 wt.-%, more preferably 0.01 to 0.4 wt.-%, even more preferably 0.05 to 0.3 wt.-%, most preferably 0.1 to 0.2 wt.-%.

Surfactant C, namely an alkyl sulfate, alkyl sarcosinate, or alkyl taurate, preferably an alkyl sarcosinate or an alkyl taurate, most preferably sodium myristoyl sarcosinate, is contained in the composition preferably within a range of 0.001 to 0.5 wt.-%, more preferably 0.01 to 0.1 wt.-%, even more preferably 0.02 to 0.08 wt.-%, most preferably 0.03 to 0.05 wt.-%.

According to the invention, the most preferred anionic surfactants mixture comprises or consists of: 0.2 to 0.3 wt.-% sodium lauryl sulfate as surfactant A, 0.1 to 0.2 wt.-% sodium methyl cocoyl taurate as surfactant B, and 0.03 to 0.05 wt.-% sodium myristoyl sarcosinate as surfactant C.

In an alternative preferred embodiment of the invention the composition contains only one anionic surfactant, namely only an alkyl sulfate such as sodium lauryl sulfate (SDS). In a preferred embodiment the composition contains next to 0.001 to 1 wt.-%, more preferably 0.01 to 0.5 wt.-%, sodium lauryl sulfate no other anionic surfactant. Such a composition is still effective in the treatment and/or prevention of a corona virus infection. However, the composition is slightly less effective as compared to a composition comprising a combination of the at least two anionic surfactants A and B (and optionally C) and is also more intensively foaming upon application so that the overall foaming behavior is less convenient for the patient. Also this alternative composition of the invention is topically administered to the mucous membranes of the (upper) respiratory tract including the nose, mouth (oral cavity) and/or throat (pharynx). All further additional features and limitations described herein are valid and applicable to this alternative embodiment as well.

In an embodiment, the composition further comprises surfactants selected from non-ionic, cationic or amphoteric surfactants. It is also possible that the composition comprises further anionic surfactants next to surfactants A, B, and C as specified herein. Suitable surfactants are described in "Cosmetic Formulation of Skin Care Products", Draelos et al., Taylor & Francis Group, 2006.

Suitable non-ionic surfactants are selected from polyoxyethylene fatty acid ethers, polyglycerol ethers of fatty acids, polyglycerol esters of fatty acids, $C_4$-$C_{26}$ fatty alcohol ethoxylates, alkylphenol ethoxylates, ethoxylated amines/amides, glycerol $C_4$-$C_{26}$ fatty acid amides, glycerol $C_4$-$C_{26}$ fatty acid esters, sorbitol fatty acid esters, and mixtures thereof. The prefix "$C_x$-$C_y$" denotes the number of carbon atoms of the respective functional group. Non-limiting examples of a $C_4$-$C_{26}$ fatty alcohol ethoxylates are pentaethylene glycol monododecyl ether (also referred to as C12E5), hexaethylene glycol monododecyl ether (C12E6), heptaethylene glycol monododecyl ether (C12E7), and octaethylene glycol monodecyl ether (C12E8). Non-limiting examples of alkylphenol ethoxylates are Triton X-100® (octyl phenol ethoxylate) and Nonidet P-40® (4-nonylphenol ethoxylate). Non-limiting examples of ethoxylated amines/amides are polyethoxylated tallow amine, cocamide monoethanolamine, and cocamide diethanolamine. Non-limiting examples of glycerol $C_4$-$C_{26}$ fatty acid esters are glycerol monostearate and glycerol monolaurate. Non-limiting examples of sorbitol fatty acid esters are sorbitan monolaurate, sorbitan monostearate and sorbitan tristearate.

Additional anionic surfactants useful herein include alkyl ether sulfates having the formula $RO(C_2H_4O)_xSO_3M$ wherein R is a $C_4$-$C_{26}$ alkyl or $C_4$-$C_{26}$ alkenyl, x is 1 to 10, and M is a water-soluble cation such as ammonium, sodium, potassium and triethanolamine. The alkyl ether sulfates useful in the present invention are condensation products of ethylene oxide and monohydric alcohols having about 4 to about 26 carbon atoms. Preferably, R is $C_{14}$-$C_{16}$ alkyl or $C_{14}$-$C_{18}$ alkenyl in the alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized. Specific examples of alkyl ether sulfates of the present invention are sodium coconut alkyl trioxyethylene sulfate; lithium tallow alkyl trioxyethylene sulfate; sodium tallow alkyl hexaoxyethylene sulfate; and sodium lauryl ether sulfate. Additional examples of anionic surfactants which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Further anionic surfactants are amino acid surfactants comprising alkyl glutamates such as sodium cocoylglutamate/disodium cocoylglutamate, alkyl glycinate, alkyl alaninate, such as sodium cocoylalaninate and mixtures thereof.

Cationic surfactants comprise primary, secondary tertiary amines, such as octenidine dihydrochloride, and quaternary ammonium salts, such as cetrimonium bromide, cetlypyridinium chloride, benzalkonium chloride, benzethonium chloride, dimethyldioctadecylammonium chloride and dioctadecyldimethylammonium bromide.

Amphoteric surfactants have an anionic and a cationic functional group. Examples of amphoteric surfactants are derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Specific examples of amphoteric surfactants are sodium 3-dodecylaminopropionate, sodium 3-dodecylaminopropane sulfonate, and N-alkyltaurines such as the one prepared by reacting dodecylamine with sodium isethionate. Particularly preferred amphoteric surfactants are betaines such as, for example, coco-amidopropyl betaines. The amphoteric surfactant component may be present in the composition in an amount ranging from about 5 to about 15% by weight, and preferably from about 9 to about 12% by weight, based on the weight of the composition.

It is preferred that the total amount of all surfactants contained in the composition of the invention is 15 wt.-% or less, preferably 10 wt.-% or less, more preferably 5 wt.-% or less, and most preferably 1 wt.-% or less. It is also preferred that the composition of the invention contains next to anionic surfactants, and in particular next to the anionic surfactants A, B and C as specified herein, no other surfactants at all, in particular no non-ionic, cationic and/or amphoteric surfactants. It was surprisingly found that the compositions are effective even with such a low total amount of surfactants.

In an embodiment, the composition comprises 0.001 to 5 wt.-% of a polyalcohol selected from erythritol, arabitol, lactitol, maltitol, mannitol, sorbitol, xylitol, and mixtures thereof. Polyalcohols can act as flavoring agents, in particular as sweeteners or masking agents that mask an otherwise unpleasant taste while at the same time minimizing or preventing tooth decay. Thus, the use of polyalcohols, such as xylitol, has the bonus effect that tooth decay due to dental caries is minimized and/or prevented, as cariogenic bacteria of the family *Streptococcus mutans* cannot metabolize polyalcohols. It is preferred that the composition comprises sorbitol and/or xylitol.

The composition may comprise 0.001 to 60 wt.-% ethanol. In an alternative embodiment, the composition of the present composition does not comprise ethanol. Ethanol has disinfectant and antiviral properties. The mouth washes and compositions for spraying of the prior art that are believed to be effective as antiviral compositions all contain ethanol. It is evident from Steinmann et al., The Journal of Infectious Diseases 2020, XX, pp 1-4 that only those compositions containing ethanol show in vitro activity against SARS-CoV-2. In view thereof, it was unexpected that the present composition is effective in the treatment and prevention of a virus infection, in particular in the treatment and prevention of a Corona virus infection, even in the absence of ethanol. Thus, it was surprising that the present composition that does not comprise ethanol is still an effective antiviral composition.

The composition may additionally contain a flavoring agent. Non-limiting examples of flavoring agents are sweeteners and essential oils. Sweeteners can be polyalcohols, aspartame, saccharin, and corn syrup. Non-limiting examples of essential oils include menthol, peppermint oil, and spearmint oil. In an embodiment, the composition comprises 0.001 to 5 wt.-% of an essential oil selected from eucalyptol, thymol, menthol, anise oil, fennel oil, and levomenthol. These essential oils can have additional beneficial properties and act as antiviral and antipuritic agents.

In an embodiment, the composition further comprises 0.001 to 20 wt.-% of a water-soluble zinc salt selected from the group consisting of zinc-L-pyrrolidone-carboxylate (zinc PCA), zinc acetate, zinc chloride, zinc histidine, zinc gluconate, zinc aspartate, zinc citrate, zinc sulfate, zinc lactate and mixtures thereof.

The additional presence of zinc ions has been found to further increase the antiviral activity of the present invention. Zinc PCA is particularly effective and preferred.

The water-soluble zinc salt also encompasses solvates (such as hydrates) of the respective zinc salts. It is preferred that the composition comprises water. Therefore, it is not particularly relevant which specific solvate is used.

In a preferred embodiment, the composition comprises the water-soluble zinc salt in an amount of 0.01 to 10 wt.-%, 0.05 to 5 wt.-% or 0.05 to 1 wt.-%, preferably in an amount of 0.05 to 0.5 wt.-%. Containing water-soluble zinc salts, preferably zinc PCA, within these ranges the compositions of the invention are surprisingly significantly effective in the treatment and/or prevention of corona virus infections.

In an embodiment, the composition comprises a transferrin, preferably lactoferrin. These proteins can further enhance the antiviral properties of the present composition.

In an embodiment, the composition comprises a film-forming polymer selected from carrageenan, carboxymethyl cellulose (CMC) and pharmaceutically acceptable salts thereof, hydroxypropyl methylcellulose (HPMC), ethyl cellulose, methyl cellulose, hydroxyethyl cellulose, hydroxypropyl cellulose, hyaluronic acid and pharmaceutically acceptable salts thereof, copolymers of methyl vinyl ether and maleic acid, and pharmaceutically acceptable salts thereof, carboxymethyl chitin, polyvinylpyrrolidone, chitosan, and mixtures thereof.

Non-limiting examples of the above pharmaceutically acceptable salts encompass the salts with calcium, sodium, potassium, and mixtures thereof.

Pharmaceutically acceptable salts of hyaluronic acid comprise the earth metal salts, such as the sodium and potassium salt.

It is believed that the present invention additionally functions by forming a protective layer of the composition according to the present invention on the mucous membrane in the mouth, throat and/or nose (i.e. in the upper respiratory tract). This antiviral drug protective layer effectively prevents infection with a virus by droplet infection in subjects not yet infected. In addition, the composition also reduces the virus count in the respiratory tract and in addition, a protective layer is formed so that a subject already infected is less infectious to other subjects, thereby also preventing further infections.

The copolymer of polyvinyl ether and maleic acid is preferable an alternating copolymer. It is to be understood that the polymer is derived from monomer units of methyl vinyl ether and maleic acid or maleic anhydride and the copolymer is also called poly(methyl vinyl ether-co-maleic acid). This polymer can be obtained by e.g. radical polymerization of the monomer units and copolymers of methyl vinyl ether and maleic acid are commercially available as Gantrez™ S polymer (International Nomenclature of Cosmetic Ingredients: PVM/MA copolymer; Ashland Inc.).

Pharmaceutically acceptable salts of this copolymer can be alkali metals and/or earth alkali metals. Thus, the salts can be selected from lithium, sodium, potassium, magnesium, calcium, and mixtures thereof. It is preferred that the salt is a sodium/calcium salt. Calcium sodium copolymer of poly(methyl vinyl ether-co-maleic acid) are commercially available as Gantrez™ MS-955 polymer (International Nomenclature of Cosmetic Ingredients: calcium/sodium PVM/MA copolymer Ashland Inc.).

In an embodiment, the composition comprises the film forming polymer in an amount of 0.01 to 10 wt.-%, 0.1 to 5 wt.-% or 1 to 2 wt.-%, preferably in an amount of 0.5 to 3 wt.-%.

In an embodiment, the composition further comprises a water-insoluble zinc salt. In an embodiment, the water-insoluble zinc salt is present in an amount of 0.001 to 20 wt.-%. In a preferred embodiment, the composition comprises the water-insoluble zinc salt in an amount of 0.01 to 10 wt.-%, 0.05 to 5 wt.-% or 0.05 to 1 wt.-%, preferably in an amount of 0.05 to 0.5 wt.-%. Containing water-insoluble zinc salts within these ranges the compositions of the invention are surprisingly significantly effective in the treatment and/or prevention of corona virus infections.

In yet another embodiment, the water-insoluble zinc salt is zinc oxide.

In an embodiment, the composition further comprises an additional active ingredient selected from menthol, lactoferrin, sorbitol, xylitol, saccharin, and mixtures thereof. These ingredients can have anti-inflammatory properties and/or protective properties of the skin and further enhance treatment and/or prevention of a virus infection. These additional active ingredients are preferably present in an amount of 0.001 to 10 wt.-%, 0.01 to 5 or 0.05 to 2 wt.-%.

In another embodiment, the composition may comprise preservatives, such as benzoic acid, phenoxyethanol, citric acid, lactic acid, ascorbic acid, tocopherol, as well as pharmaceutically acceptable salts thereof.

In an embodiment, the composition may comprise hydroxyapatite (HAP) in order to further increase the efficacy in treating and/or preventing corona virus infections. Hydroxyapatite is a naturally occurring inorganic mineral having the general formula $Ca_5(PO_4)_3(OH)$. In a preferred embodiment, the hydroxyapatite is not doped with any ions, i.e. the hydroxyapatite has less than 1 wt-% of its ions ($Ca^{2+}$, $PO_4^{3-}$ and $OH^-$) replaced by different ions.

Hydroxyapatite is naturally occurring but can also be obtained by processes known to the skilled person. For example, hydroxyapatite can be obtained by the reaction of a calcium salt, such as $CaCl_2$) or $CaNO_3$, with a phosphate salt, such as $(NH_4)_3PO_4$, $Na_3PO_4$ or $NaHPO_4$, in water at a temperature of 10 to 100° C. or in an autoclave at temperatures above 100° C.

Hydroxyapatite can i.a. be doped with the following ions: $CO_3^{2-}$, $Ag^+$, $Mg^{2+}$, $Cu^{2+}$. Therefore, in a non-limiting example, the term "hydroxyapatite (HAP)" is to be understood to encompass compositions doped with the above ions and to have the following formula:

$$Ca_{10-x}M_x(PO_4)_{6-y}(CO_3)_{y+z}(OH)_{2-z},$$

wherein M Cu, Mg or Ag, x is a number between 0 and 0.6, y is a number between 0 and 0.9, and z is a number between 0 and 0.32.

In a preferred embodiment, x is a number between 0.0055 and 0.6, y is a number between 0.065 and 0.9, and z is a number between 0 and 0.32.

This doping with ions can be obtained by the addition of suitable salts, such as $MgCl_2$, during the formation of the hydroxyapatite.

In a non-limiting example, the hydroxyapatite has a volume-based particle size $X_{50}$ of 1 to 1000 nm, 10 to 500 nm, 20 to 300 nm 30 to 200 nm or 50 to 150 nm, preferably 30 to 200 nm. The $X_{50}$ value can be measured by laser diffraction using a Mastersizer 2000 (Malvern Instruments GmbH) according to DIN ISO 14887:2010.

In a non-limiting example, the hydroxyapatite has a crystalline form having a hexagonal crystal lattice with an a-axis of 0.930 to 0.950 nm, preferably of 0.933 to 0.948 nm, particularly preferably of 0.936 to 0.945 nm and a length of the c-axis of 0.680 bis 0.700 nm, preferably of 0.682 to 0.696 nm, particularly preferably of 0.685 to 0.692 nm. The lattice parameters can be determined by X-ray powder diffraction using a diffractometer (Bruker D8) and Rietveld analysis.

In an embodiment the composition of the invention does not contain zinc hydroxyapatite (Zn HAP). This also includes embodiments comprising HAP, but only HAP that does not contain zinc ions (zinc-free HAP). In an alternative embodiment, the composition of the invention does not contain hydroxyapatite (HAP) at all. In other words, the composition of the invention may also be HAP-free.

A particularly suitable composition according to the present invention is the following composition that comprises:

0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof, 0.001 to 1 wt.-% of a total amount of anionic surfactants, comprising at least two anionic surfactants A and B in a weight ratio NB from 10/1 to 1.1/1, preferably 7/1 to 1.1/1, wherein surfactant A is an alkyl sulfate and surfactant B is selected from alkyl sulfates, alkyl sarcosinates, and alkyl taurates, and 0.001 to 5 wt.-% of a polyalcohol selected from erythritol, arabitol, lactitol, maltitol, mannitol, sorbitol, xylitol, and mixtures thereof.

A further suitable composition according to the present invention is the following composition that comprises:

0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof, 0.001 to 0.5 wt.-% of a total amount of anionic surfactants, comprising three anionic surfactants A, B, and C, wherein surfactant A is an alkyl sulfate, surfactant B is an alkyl taurate, and surfactant C is an alkyl sarcosinate, and 0.001 to 5 wt.-% of a polyalcohol selected from erythritol, arabitol, lactitol, maltitol, mannitol, sorbitol, xylitol, and mixtures thereof.

All preferred embodiments as described hereinabove are valid for and applicable to these particularly suitable compositions as well.

In an embodiment, the composition is a liquid topical composition such as a cosmetic, medical, or pharmaceutical composition.

All compositions of the invention as described herein are preferably topically administered to the mucous membranes of the (upper) respiratory tract including nose, mouth (oral cavity) and/or throat (pharynx). Most preferably the compositions of the invention are topically applied to the throat (pharynx), such as by gargling or any other kind of distribution or administration. Preferably they are topically applied to the mucous membranes as a mouth rinse or as an aerosol by spraying, preferably as a mouth rinse. Mouth rinses suitable according to the present invention are mouth rinses applied by flushing/rinsing the mouth, nose and/or throat, e.g. by gargling. They are also named gargle rinses or oral rinses (suitable for flushing and/or gargling). The application as a mouth rinse or as a spray/aerosol has the further advantage that a uniform, homogenous and long-lasting protective layer on the mucous membranes is formed. In addition, protection can be achieved on a large area, thereby leading to an even better protection.

The spraying device can be used to apply the composition to the mucous membranes in the mouth (oral cavity), throat (pharynx) or nose. It is preferred that the spraying device is used to apply the composition to the mucous membranes in the mouth or pharynx. It is particularly preferred that the spraying device contains a means for (pre-)determining the amount of the composition that is applied.

Suitable pump spraying devices are known (see i.a. U.S. Pat. No. 4,245,967) and are commercially available as "throat sprays". Such sprays are usually used to treat sore throats caused by bacterial infections of the throat and mucous membrane and/or decrease any symptoms of such infections. Such sprays can contain an antibacterial ingredient to fight the bacterial infection as well as an analgesic to decrease any symptoms of pain and/or soreness.

Spraying devices commonly comprise a feed chamber and an outlet through which the composition is sprayed in a predetermined amount by a suitable means for spraying the composition through a nozzle. It is preferred that the spraying device is a pump spraying device. Such a pump spray contains an atomizer nozzle that disperses the liquid composition as a fine aerosol. This aerosol covers the area on which it is sprayed and forms a thin film.

The compositions of the invention as described herein are preferably administered several times per day, such as 1 to 5 times, more preferably 2 to 4 times, most preferably around 2 to 3 times, in particular before and/or after (potential) contacts with the virus and/or virus infected subjects. In case of use as a mouth rinse it is preferred to apply the composition by gargling (rinsing the mouth and in particular the throat/pharynx). A suitable volume to be applied is from 5 to 25 ml, preferably 10 to 20 ml and in particular 15 ml, each per application. The application time typically ranges from 10 seconds to 120 seconds, preferably from 30 seconds to 90 seconds, and most preferably is about 60 seconds, each per application. The compositions may be administered shortly before and/or after social contacts. In this way the compositions of the invention assist in providing the user/patient with an increased social freedom and convenience and effectively helps to minimize further spreading of the virus. Thus, the invention helps to limit the incidence figures of corona virus infections eventually.

The compositions of the invention are useful for both, the treatment as well as the prevention of a virus infection. In a preferred embodiment, the composition is used for the prevention (prophylaxis) of a virus infection.

In an embodiment, the virus belongs to the family of Coronaviridae, and preferably is SARS-CoV-2. Alternatively, the virus is a common human corona virus selected from 229E, NL63, 0043 and HKU1.

EXAMPLES

Example 1

The composition comprising the components as depicted below in Table 1 was obtained by mixing the components.

TABLE 1

Ingredients of Example 1

| Ingredients | Amount in wt.- % |
|---|---|
| Aqua | add. 100 |
| Sorbitol | 15 |
| Xylitol | 1.5 |
| Hydroxyapatite | 0.62 |
| Phenoxyethanol | 0.3 |
| Sodium Benzoate | 0.15 |
| Zinc PCA | 0.3 |
| PEG-40 hydrogenated castor oil | 0.7 |
| Cellulose gum | 0.6 |
| Sodium lauryl sulfate | 0.3 |
| Sodium myristoyl sarcosinate | 0.03 |
| Sodium methyl cocoyl taurate | 0.1 |
| Sodium saccharin | 0.05 |
| Lactoferrin | 0.03 |
| Sodium hyaluronate | 0.1 |
| Phosphoric acid | 0.1 |

Example 2

The composition comprising the components as depicted below in Table 2 was obtained by mixing the components.

TABLE 2

Ingredients of Example 2

| Ingredients | Amount in wt.- % |
|---|---|
| Aqua | add. 100 |
| Sorbitol | 15 |
| Xylitol | 1.5 |
| Phenoxyethanol | 0.3 |
| Sodium Benzoate | 0.15 |
| Zinc PCA | 0.3 |
| PEG-40 hydrogenated castor oil | 0.7 |
| Cellulose gum | 0.6 |
| Sodium lauryl sulfate | 0.8 |
| Sodium myristoyl sarcosinate | 0.03 |
| Sodium methyl cocoyl taurate | 0.1 |
| Sodium saccharin | 0.05 |
| Lactoferrin | 0.03 |
| Sodium hyaluronate | 0.1 |
| Phosphoric acid | 0.1 |

Example 3

The composition of Example 1 was measured in a quantitative suspension test (80% dilution) for antiviral efficacy against bovine Corona virus (BCoV) under dirty conditions in vitro according to DIN EN 14476.

After treatment with a composition of Example 1 and a contact time of 30 sec, the virus load of bovine Corona virus was reduced to an undetectable level (log steps 4.38 LVP (Large Volume Procedure)). Thus, the corona virus was completely inactivated by the composition of Example 1.

Example 4

A clinical trial was conducted to obtain in vivo data using the composition of Example 1. In total, 12 adult hospitalized patients with positive SARS-CoV-2 tests were recruited. Directly before and 5 minutes after gargling, pharyngeal swabs using a standardized protocol were taken and sent to an experienced laboratory for clinical diagnostics to perform real time polymerase chain reaction (rt PCR) analyzing the samples for cycle threshold (CT) detecting SARS-CoV-2. According to a rough estimation of the slope of the calibration curve, an increase of post CT values by 1, 2, 3 and 4 cycles correspond to a decrease of viral load of about 55%, 73%, 86% and 93%, respectively.

| Patients ID | CT before gargling | CT after gargling | Decrease Virus Load (%) |
|---|---|---|---|
| 1 | 34 | 36 | 73 |
| 2 | 32 | 33 | 55 |
| 3 | 30 | 34 | 93 |
| 4 | 24 | 26 | 73 |
| 5 | 32 | 35 | 86 |
| 6 | 26 | 32 | 99 |
| 7 | 25 | 27 | 73 |
| 8 | 28 | 30 | 73 |
| 9 | 24 | 24 | 0 |
| 10 | 33 | 33 | 0 |
| 11 | 34 | No virus detectable | 100 |
| 12 | 34 | No virus detectable | 100 |

It becomes evident from the data in the table that the composition of Example 1 significantly reduces the virus load of the patients involved in the study. Two patients (ID 9 and 10) were non-responders. However, even if the virus load in these patients after gargling was not decreased, it remained constant. Thus, the composition of Example 1 in these patients was effective at least in that the virus load did not increase. On the other hand, in two patients (ID 11 and 12) no virus load was detectable after gargling meaning a decrease in virus load of 100%. Thus, the composition of Example 1 is shown to be effective in the treatment and prevention of the corona virus infection.

The invention claimed is:

1. A composition comprising at least two anionic surfactants A and B in a weight ratio A/B from 10/1 to 1.1/1, wherein surfactant A is an alkyl sulfate and surfactant B is selected from alkyl sulfates, alkyl sarcosinates, and alkyl taurates, wherein the total amount of anionic surfactants in the composition is 1 wt.-% or less.

2. The composition according to claim 1, further comprising an anionic surfactant C selected from alkyl sulfates, alkyl sarcosinates, and alkyl taurates, wherein the weight ratio A/C is from 16/1 to 1.1/1.

3. The composition according to claim 2, comprising sodium lauryl sulfate as surfactant A, sodium methyl cocoyl taurate as surfactant B, and sodium myristoyl sarcosinate as surfactant C, each in an amount of 0.001 to 0.5 wt.-%.

4. The composition according to claim 1, further comprising 0.001 to 5 wt.-% of a polyalcohol selected from erythritol, arabitol, lactitol, maltitol, mannitol, sorbitol, xylitol, and mixtures thereof.

5. The composition according to claim 4, wherein the polyalcohol is sorbitol and/or xylitol.

6. The composition according to claim 1, wherein the total amount of anionic surfactants in the composition is from 0.001 to 1 wt.-%.

7. The composition according to claim 1, wherein the total amount of anionic surfactants in the composition is from 0.1 to 0.5 wt.-%.

8. The composition according to claim 1, further comprising 0.001 to 5 wt.-% of an essential oil selected from eucalyptol, thymol, menthol, anise oil, fennel oil, and levomenthol.

9. The composition according to claim 1, further comprising 0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof.

10. The composition according to claim 1, wherein the composition comprises a transferrin.

11. The composition according to claim 10, wherein the transferrin is lactoferrin.

12. The composition according to claim 1, further comprising a film-forming polymer selected from carrageenan, carboxymethyl cellulose (CMC) and pharmaceutically acceptable salts thereof, hydroxypropyl methylcellulose (HPMC), ethyl cellulose, methyl cellulose, hydroxyethyl cellulose, hydroxypropyl cellulose, hyaluronic acid and pharmaceutically acceptable salts thereof, copolymers of methyl vinyl ether and maleic acid, and pharmaceutically acceptable salts thereof, carboxymethyl chitin, polyvinylpyrrolidone, chitosan, and mixtures thereof.

13. The composition according to claim 1, further comprising a water-insoluble zinc salt.

14. The composition according to claim 1, wherein the composition is a mouth rinse or an aerosol.

15. The composition according to claim 1, wherein the virus is SARS-CoV-2 or a human corona virus selected from 229E, NL63, OC43 and HKU1.

16. A kit of parts comprising the composition according to claim 1 and a spraying device or a mouth rinse device or a gargling device, for applying the composition to the mucous membranes of the nose, mouth and/or throat.

17. A composition comprising 0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof, 0.001 to 1 wt.-% of a total amount of anionic surfactants, comprising at least two anionic surfactants A and B in a weight ratio A/B from 10/1 to 1.1/1, wherein surfactant A is an alkyl sulfate and surfactant B is selected from alkyl sulfates, alkyl sarcosinates, and alkyl taurates, and 0.001 to 5 wt.-% of a polyalcohol selected from erythritol, arabitol, lactitol, maltitol, mannitol, sorbitol, xylitol, and mixtures thereof.

18. A method for treating a corona virus infection or reducing the probability of a corona virus infection, comprising administering a composition to a subject, wherein the composition comprises at least two anionic surfactants A and B in a weight ratio A/B from 10/1 to 1.1/1, wherein surfactant A is an alkyl sulfate and surfactant B is selected from alkyl sulfates, alkyl sarcosinates, and alkyl taurates, wherein the total amount of anionic surfactants in the composition is 1 wt.-% or less.

19. The method of claim 18, wherein the composition comprises:

0.001 to 20 wt.-% of a water-soluble zinc salt selected from the group consisting of zinc-L-pyrrolidone-carboxylate, zinc acetate, zinc chloride, zinc histidine, zinc gluconate, zinc aspartate, zinc citrate, zinc sulfate, zinc lactate and mixtures thereof, 0.001 to 1 wt.-% of a total amount of anionic surfactants, comprising surfactants A and B in a weight ratio A/B from 10/1 to 1.1/1, wherein surfactant A is an alkyl sulfate and surfactant B is selected from alkyl sulfates, alkyl sarcosinates, and alkyl taurates, and 0.001 to 5 wt.-% of a polyalcohol selected from erythritol, arabitol, lactitol, maltitol, mannitol, sorbitol, xylitol, and mixtures thereof.

20. The method of claim 18, wherein the composition is topically administered to a mucous membrane of the nose, mouth and/or throat of the subject.

*    *    *    *    *